United States Patent
Patel et al.

(10) Patent No.: US 10,322,116 B2
(45) Date of Patent: Jun. 18, 2019

(54) PHARMACEUTICAL COMPOSITIONS COMPRISING ANTIBACTERIAL AGENTS

(71) Applicant: WOCKHARDT LIMITED, Aurangabad (IN)

(72) Inventors: Mahesh Vithalbhai Patel, Aurangabad (IN); Sachin Bhagwat, Aurangabad (IN); Jaykumar Satwaji Satav, Hingoli (IN); Hemant Narendra Khande, Nashik (IN); Prashant Ratnakar Joshi, Parbhani (IN); Snehal Rameshwar Palwe, Buldhana (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 15 days.

(21) Appl. No.: 15/323,631

(22) PCT Filed: Jan. 20, 2015

(86) PCT No.: PCT/IB2015/050421
§ 371 (c)(1),
(2) Date: Jan. 3, 2017

(87) PCT Pub. No.: WO2015/110950
PCT Pub. Date: Jul. 30, 2015

(65) Prior Publication Data
US 2017/0202813 A1    Jul. 20, 2017

(30) Foreign Application Priority Data
Jan. 21, 2014    (IN) .......................... 193/MUM/2014

(51) Int. Cl.
*A61K 31/439*    (2006.01)
*A61K 31/407*    (2006.01)

(52) U.S. Cl.
CPC .......... *A61K 31/439* (2013.01); *A61K 31/407* (2013.01)

(58) Field of Classification Search
CPC .................................................. A61K 31/439
USPC ....................................................... 514/300
See application file for complete search history.

(56) References Cited

U.S. PATENT DOCUMENTS

| | | | |
|---|---|---|---|
| 9,132,133 B2 * | 9/2015 | Patel | A61K 31/4545 |
| 9,433,613 B2 * | 9/2016 | Patel | A61K 45/06 |
| 9,636,331 B2 * | 5/2017 | Patel | A61K 31/439 |
| 2013/0225554 A1 | 8/2013 | Maiti et al. | |

FOREIGN PATENT DOCUMENTS

| | | |
|---|---|---|
| CA | 2874279 A1 | 12/2013 |
| WO | WO/2013/030733 | 3/2013 |
| WO | WO/2014/108872 | 7/2014 |

OTHER PUBLICATIONS

Sugar et al., Interactions of Itraconazole with Amphotericin B in the Treatment of Murine Invasive Candidiasis, The Journal of Infectious Diseases 1988, vol. 177, pp. 1660-1663.
Maesaki et al. Effects of antifungal agent combinations administered simultaneously and sequentially against Aspergillus fumigatus. Antimicrobial Agents and Chemotherapy, Dec. 1994, pp. 2843-2845.
Bergogne-Berezin. Mechanisms and clinical relevance of antagonism between beta-lactam antibiotics. Chemioterapia. Feb. 1985;4(1):47-52.
Wanted: a reward for antibiotic development-Nature Biotechnology vol. 36 No. 7 Jul. 2018, p. 555.
Krisztina et al. [p. 4946, at col. 1, para. 4]. Minireview Carbapenerns: Past, Present, and Future. Antimicrobial Agents and Chemotherapy, Nov. 2011, p. 4943-4960.
METC Protocol NABOGO version 2.0 d.d. Oct. 5, 2017. Academical Medical Center (AMC)—Public Health Service (GGD) Amsterdam.
UK Standards for Microbiology Imvestigations Issued by the Standards Unit, Microbiology Services, PHB Bacteriology | B 60 | Issue No. 2.1 | Issue date: Sep. 20, 2016 | p. 1 of 41.
Nature Biotechnology vol. 36 No. 7 Jul. 2018, p. 555.

* cited by examiner

*Primary Examiner* — Charanjit Aulakh
(74) *Attorney, Agent, or Firm* — Bio Intellectual Property Services LLC; O. (Sam) Zaghmout

(57) ABSTRACT

A pharmaceutical compositions comprising: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutical acceptable derivative thereof, are disclosed.

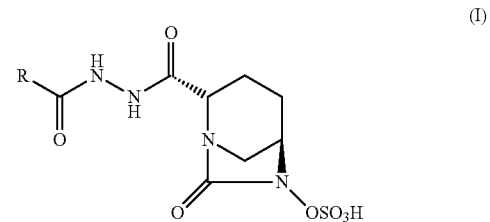

(I)

24 Claims, No Drawings

PHARMACEUTICAL COMPOSITIONS COMPRISING ANTIBACTERIAL AGENTS

RELATED PATENT APPLICATION

This application claims priority to Indian Patent Application No. 193/MUM/2014 filed on Jan. 21, 2014, the disclosures of which are incorporated herein by reference in its entirety as if fully rewritten herein.

FIELD OF THE INVENTION

The invention relates to antibacterial compositions and methods for treating or preventing bacterial infections.

BACKGROUND OF THE INVENTION

Bacterial infections continue to remain one of the major causes contributing towards human diseases. One of the key challenges in treatment of bacterial infections is the ability of bacteria to develop resistance to one or more antibacterial agents over time. Examples of such bacteria that have developed resistance to typical antibacterial agents include: Penicillin-resistant *Streptococcus pneumoniae*, Vancomycin-resistant *Enterococci*, and Methicillin-resistant *Staphylococcus aureus*. The problem of emerging drug-resistance in bacteria is often tackled by switching to newer antibacterial agents, which can be more expensive and sometimes more toxic. Additionally, this may not be a permanent solution as the bacteria often develop resistance to the newer antibacterial agents as well in due course. In general, bacteria are particularly efficient in developing resistance, because of their ability to multiply very rapidly and pass on the resistance genes as they replicate.

The persistent exposure of bacterial strains to a multitude of beta-lactam antibacterial agents has led to overproduction and mutation of beta-lactamases. These new extended spectrum beta-lactamases (ESBL) are capable of hydrolyzing penicillins, cephalosporins, monobactams and even carbapenems. Such a wide spread resistance to many of the existing beta-lactam antibacterial agents, either used alone or in combination with other agents, is posing challenges in treating serious bacterial infections.

Therefore, there is a need for development of newer ways to treat infections that are becoming resistant to known therapies and methods. Surprisingly, it has been found that compositions comprising a carbapenem antibacterial agent and certain nitrogen containing bicyclic compounds (disclosed in PCT/IB2012/054290) exhibit unexpectedly synergistic antibacterial activity, even against highly resistant bacterial strains.

SUMMARY OF THE INVENTION

Accordingly, there are provided pharmaceutical compositions comprising: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof:

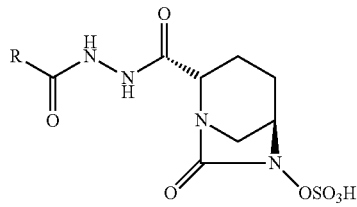

Formula (I)

wherein, R is heterocycloalkyl.

In one general aspect, there are provided pharmaceutical compositions comprising: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof; wherein a compound of Formula (I), or a stereoisomer or a pharmaceutically acceptable derivative thereof is present in the composition in an amount from about 0.25 gram to about 4 gram per gram of the carbapenem antibacterial agent selected from imipenem, meropenem, ertapenem, doripenem, or a pharmaceutically acceptable derivative thereof.

In yet another general aspect, there are provided methods for treating or preventing a bacterial infection in a subject, said methods comprising administering to said subject an effective amount of a pharmaceutical composition comprising: (a) a carbapenem antibacterial agent selected from imipenem, meropenem, ertapenem, doripenem or a pharmaceutically acceptable derivative thereof; and (b) a compound of Formula (I), or a stereoisomer or a pharmaceutically acceptable derivative thereof.

In another general aspect, there are provided methods for treating or preventing a bacterial infection in a subject, said methods comprising administering to said subject an effective amount of a pharmaceutical composition comprising: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof; wherein a compound of Formula (I), or a stereoisomer or a pharmaceutically acceptable derivative thereof is present in the composition in an amount from about 0.25 gram to about 4 gram per gram of carbapenem antibacterial agent selected from imipenem, meropenem, ertapenem, doripenem or a pharmaceutically acceptable derivative thereof.

In yet another general aspect, there are provided methods for treating or preventing a bacterial infection in a subject, said methods comprising administering to said subject an effective amount of: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof.

In another general aspect, there are provided methods for treating or preventing a bacterial infection in a subject, said methods comprising administering to said subject an effective amount of: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof; wherein a compound of Formula (I), or a stereoisomer or a pharmaceutically acceptable derivative thereof is administered in an amount from about 0.25 gram to about 4 gram per gram of the carbapenem antibacterial agent selected from imipenem, meropenem, ertapenem, doripenem or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety as if fully rewritten herein.

The inventors have surprisingly discovered that a pharmaceutical composition comprising: (a) a carbapenem antibacterial agent selected from imipenem, meropenem, ertapenem, doripenem or a pharmaceutically acceptable derivative thereof, and (b) a compound of Formula (I) or a stereoisomer or a pharmaceutically acceptable derivative thereof exhibits unexpectedly improved antibacterial efficacy, even against highly resistant bacteria, including those producing extended spectrum beta-lactamase enzymes (ESBLs).

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of other floras, which are not desirable. The term "infection" includes infection caused by bacteria.

The term "treat", "treating" or "treatment" as used herein refers to administration of a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions, or one or more of pharmaceutically active ingredients discussed herein, with or without additional pharmaceutically active or inert ingredients, in order to: (i) reduce or eliminate either a bacterial infection, or one or more symptoms of a bacterial infection, or (ii) retard progression of a bacterial infection, or one or more symptoms of a bacterial infection, or (iii) reduce severity of a bacterial infection, or one or more symptoms of a bacterial infection, or (iv) suppress clinical manifestation of a bacterial infection, or (v) suppress manifestation of adverse symptoms of a bacterial infection.

The terms "pharmaceutically effective amount" or "therapeutically effective amount" or "effective amount" as used herein refer to an amount, which has a therapeutic effect or is the amount required to produce a therapeutic effect in a subject. For example, a "therapeutically effective amount" or "pharmaceutically effective amount" or "effective amount" of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). Such effective amount depends on several factors, including but not limited to, the microorganism (e.g. bacteria) involved, characteristics of the subject (for example height, weight, sex, age and medical history), severity of infection and particular type of the antibacterial agent used. For prophylactic treatments, a prophylactically effective amount is that amount which would be effective in preventing the bacterial infection.

The term "administration" or "administering" refers to and includes delivery of a composition, or one or more pharmaceutically active ingredients to a subject, including for example, by any appropriate method, which serves to deliver the composition or its active ingredients or other pharmaceutically active ingredients to the site of infection. The method of administration may vary depending on various factors, such as for example, the components of the pharmaceutical composition or type/nature of the pharmaceutically active or inert ingredients, site of the potential or actual infection, the microorganism involved, severity of the infection, age and physical condition of the subject and a like. Some non-limiting examples of ways to administer a composition or a pharmaceutically active ingredient to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop and mouthwash. In case of a pharmaceutical composition comprising more than one ingredients (active or inert), one of the ways of administering such composition is by admixing the ingredients (e.g. in the form of a suitable unit dosage form such as tablet, capsule, solution, powder or a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term "growth" also includes maintenance of on-going metabolic processes of the microorganism, including the processes that keep the microorganism alive.

The term, "effectiveness" as used herein refers to ability of a treatment, or a composition, or one or more pharmaceutically active ingredients to produce a desired biological effect in a subject. For example, the term "antibacterial effectiveness" of a composition or of an antibacterial agent refers to the ability of the composition or the antibacterial agent to prevent or treat bacterial infection in a subject.

The term "synergistic" or "synergy" as used herein refers to the interaction of two or more agents so that their combined effect is greater than their individual effects.

The term "antibacterial agent" as used herein refers to any substance, compound, a combination of substances, or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam compound" as used herein refers to compounds containing a beta-lactam nucleus in their molecular structure.

The term "carbapenem antibacterial agent" as used herein refers to class of antibacterial agents having the following core structure:

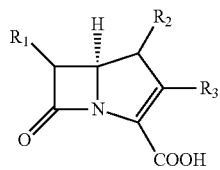

wherein, $R_1$, $R_2$ and $R_3$ are typical substituents found in the structures of carbapebems.

The term "beta-lactamase" or "beta-lactamase enzyme" as used herein refers to any enzyme or protein or any other substance that breaks down a beta-lactam ring. The term "beta-lactamase" includes enzymes that are produced by bacteria and have the ability to hydrolyse the beta-lactam ring in a beta-lactam compound, either partially or completely.

The term "extended spectrum beta-lactamase" (ESBL) as used herein includes those beta-lactamase enzymes, which are capable of conferring bacterial resistance to various beta-lactam antibacterial agents such as penicillins, cephalosporins, aztreonam and the like.

The term "beta-lactamase inhibitor" as used herein refers to a compound capable of inhibiting activity of one or more beta-lactamase enzymes, either partially or completely.

The term "colony forming units" or "CFU" as used herein refers to an estimate of number of viable bacterial cells per ml of the sample. Typically, a "colony of bacteria" refers to a mass of individual bacteria growing together.

The term "pharmaceutically inert ingredient" or "carrier" or "excipient" refers to and includes compounds or materials used to facilitate administration of a compound, for example, to increase the solubility of the compound. Typical, non-limiting examples of solid carriers include starch, lactose, dicalcium phosphate, sucrose, and kaolin. Typical, non-limiting examples of liquid carriers include sterile water, saline, buffers, non-ionic surfactants, and edible oils. In addition, various adjuvants commonly used in the art may also be included. These and other such compounds are described in literature, e.g., in the Merck Index (Merck & Company, Rahway, N.J.). Considerations for inclusion of various components in pharmaceutical compositions are described, e.g., in Gilman et al. (Goodman and Gilman's: The Pharmacological Basis of Therapeutics, 8th Ed., Pergamon Press., 1990), which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" include humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salts, pro-drugs, metabolites, esters, ethers, hydrates, polymorphs, solvates, complexes, and adducts) which, upon administration to a subject, are capable of providing (directly or indirectly) the antibacterial agent.

The term "pharmaceutically acceptable salt" as used herein refers to one or more salts of a given compound which possesses desired pharmacological activity of the free compound and which is neither biologically nor otherwise undesirable. In general, the term "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutically acceptable salts in details.

The term "heterocycloalkyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting examples of heterocycloalkyl groups include pyrrolidine, 2-oxo-pyrrolidine, imidazolidin-2-one, piperidine, oxazine, thiazine, piperazine, piperazin-2,3-dione, morpholine, thiamorpholine, azapane, and the like. The heterocycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like. The term "heterocyclyl" as used herein refers to cyclic groups in which a ring portion includes at least one heteroatom such as oxygen, nitrogen or sulfur. Heterocyclic groups include "heteroaryl" as well as "heterocycloalkyl". The term "heteroaryl" as used herein refers to a monocyclic or polycyclic aromatic hydrocarbon group wherein one or more carbon atoms have been replaced with heteroatoms selected from nitrogen, oxygen or sulfur. Typical non-limiting examples of heteroaryl group include pyridine, pyrimidine, pyrazine, pyridazine, furan, pyrrol, thiophene, and the like. The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, and the like.

The term "stereoisomer" as used herein refers to compound that has identical chemical constitution, but differ with regard to the arrangement of the atoms or groups in space. The compounds of Formula (I) may contain asymmetric or chiral centers and therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

A person of skills in the art would appreciate that various compounds described herein (including, for example a compound of Formula (I), imipenem, meropenem, ertapenem or doripenem) can exist and are often used as their pharmaceutically acceptable derivatives (such as salts, pro-drugs, metabolites, esters, ethers, hydrates, polymorphs, solvates, complexes, and adducts). Typical, non-limiting examples of pharmaceutically acceptable derivative of ertapenem include ertapenem sodium. Typical, non-limiting examples of pharmaceutically acceptable derivative of imipenem include imipenem monohydrate or imipenem hydrochloride. Typical, non-limiting examples of pharmaceutically acceptable derivative of meropenem include meropenem trihydrate. Typical, non-limiting examples of pharmaceutically acceptable derivative of doripenem include doripenem monohydrate.

In one general aspect, there are provided pharmaceutical compositions comprising: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof:

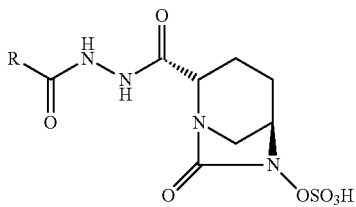

Formula (I)

wherein, R is heterocycloalkyl.

Compound of Formula (I), according to the invention can be used in various forms including as such, a stereoisomer or a pharmaceutically acceptable derivative thereof.

A compound of Formula (I) wherein 'R' is pyrrolidine, may also be known by different chemical names including the following: (a) "trans-sulfuric acid mono-[2-(N'-[(R)-pyrrolidin-3-carbonyl]-hydrazinocarbonyl)-7-oxo-1,6-diaza-bicyclo[3.2.1]oct-6-yl] ester"; (b) "(2S, 5R) sulfuric acid mono-[2-(N'-[(R)-pyrrolidin-3-carbonyl]-hydrazinocarbonyl)-7-oxo-1,6-diaza-bicyclo[3.2.1]oct-6-yl] ester"; (c) "(2S,5R)-7-oxo-6-sulphooxy-2-[N'-((R)-pyrrolidine-3-carbonyl)-hydrazinocarbonyl]-1,6-diaza-bicyclo[3.2.1]octane"; (d) "1,6-diazabicyclo[3.2.1]octane-2-carboxylic acid, 7-oxo-6-(sulfooxy)-, 2-[2-[(3R)-3-pyrrolidinylcarbonyl]hydrazide], (2S,5R)-" [CAS Registry Number: 1436862-02-0]; or (e) "1,6-diazabicyclo[3.2.1]octane-2-carboxylic acid, 7-oxo-6-(sulfooxy)-, 2-[2-[(3R)-3-pyrrolidinylcarbonyl]hydrazide], (1R,2S,5R)-" [CAS Registry Number: 1452459-94-7].

A compound of Formula (I), wherein 'R' is piperidine may also be known by different chemical names including the following: (a) "trans-sulphuric acid mono-[2-(N'-[(R)-piperidin-3-carbonyl]-hydrazinocarbonyl)-7-oxo-1,6-diaza-bicyclo[3.2.1]oct-6-yl] ester", (b) "(2S,5R)-sulphuric acid mono-[2-(N'-[(R)-piperidin-3-carbonyl]-hydrazinocarbonyl)-7-oxo-1,6-diaza-bicyclo[3.2.1]oct-6-yl] ester", or (c) "1,6-diazabicyclo [3.2.1] octane-2-carboxylic acid, 7-oxo-6-(sulfooxy)-, 2-[2-[(3R)-3-piperidinylcarbonyl]hydrazide], (1R,2S,5R)-" [CAS Registry Number: 1436861-97-0].

Compound of Formula (I) may also be used in the form of its stereoisomer or a pharmaceutically acceptable derivative thereof. Typical, non-limiting examples of stereoisomeric forms of a compound of Formula (I), wherein 'R' is pyrrolidine include the following:

(a) "1,6-diazabicyclo[3.2.1]octane-2-carboxylic acid, 7-oxo-6-(sulfooxy)-, 2-[2-[(3R)-3-pyrrolidinylcarbonyl]hydrazide], (2S,5R)-" [CAS Registry Number: 1436862-02-0];

(b) "1,6-diazabicyclo[3.2.1]octane-2-carboxylic acid, 7-oxo-6-(sulfooxy)-, 2-[2-(3-pyrrolidinylcarbonyl)hydrazide], (2S,5R)-" [CAS Registry Number: 1436862-37-1];

(c) "1,6-diazabicyclo[3.2.1]octane-2-carboxylic acid, 7-oxo-6-(sulfooxy)-, 2-[2-[(3S)-3-pyrrolidinylcarbonyl]hydrazide], (2S,5R)-" [CAS Registry Number: 1436862-38-2];

(d) "1,6-diazabicyclo[3.2.1]octane-2-carboxylic acid, 7-oxo-6-(sulfooxy)-, 2-[2-(3-pyrrolidinylcarbonyl)hydrazide], (1R,2S,5R)-" [CAS Registry Number: 1452464-05-9];

(e) "1,6-diazabicyclo[3.2.1]octane-2-carboxylic acid, 7-oxo-6-(sulfooxy)-, 2-[2-[(3R)-3-pyrrolidinylcarbonyl]hydrazide], (1R,2S,5R)-" [CAS Registry Number: 1452459-94-7]; or (f) "1,6-Diazabicyclo[3.2.1]octane-2-carboxylic acid, 7-oxo-6-(sulfooxy)-, 2-[2-[(3S)-3-pyrrolidinylcarbonyl]hydrazide], (1R,2S,5R)-" [CAS Registry Number: 1452460-79-5].

Typical, non-limiting examples of stereoisomeric forms of a compound of Formula (I), wherein 'R' is piperidine, include the following:

(a) "1,6-diazabicyclo[3.2.1]octane-2-carboxylic acid, 7-oxo-6-(sulfooxy)-, 2-[2-(3-piperidinylcarbonyl) hydrazide], (1R,2S,5R)-" [CAS Registry No.: 1452464-14-0];

(b) "1,6-diazabicyclo[3.2.1]octane-2-carboxylic acid, 7-oxo-6-(sulfooxy)-, 2-[2-[(3S)-3-piperidinylcarbonyl]hydrazide], (2S,5R)-" [CAS Registry No.: 1436862-20-2];

(c) "1,6-diazabicyclo[3.2.1]octane-2-carboxylic acid, 7-oxo-6-(sulfooxy)-, 2-[2-(3-piperidinylcarbonyl)hydrazide], (2S,5R)-" [CAS Registry No.: 1436862-19-9]; and (d) "1,6-diazabicyclo[3.2.1]octane-2-carboxylic acid, 7-oxo-6-(sulfooxy)-, 2-[2-[(3R)-3-piperidinylcarbonyl]hydrazide], (1R,2S,5R)-" [CAS Registry No.: 1436861-97-0].

Typical, non-limiting examples of suitable pharmaceutically acceptable derivatives of a compound of Formula (I) include its various salts such as a sodium, potassium, trifluroacetate or any other salt. In some embodiments, compound of Formula (I), wherein 'R' is pyrrolidine, is "1,6-diazabicyclo[3.2.1]octane-2-carboxylic acid, 7-oxo-6-(sulfooxy)-, 2-[2-[(3R)-3-pyrrolidinylcarbonyl]hydrazide], (1R,2S,5R)-, 2,2,2-trifluoroacetate (1:1)" [CAS Registry Number: 1452459-95-8].

In another general aspect, there are provided pharmaceutical compositions comprising: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof; wherein a compound of Formula (I), or a stereoisomer or a pharmaceutically acceptable derivative thereof is present in the composition in an amount from about 0.25 gram to about 4 gram per gram of carbapenem antibacterial agent selected from imipenem, meropenem, ertapenem, doripenem or a pharmaceutically acceptable derivative thereof.

Both, carbapenem antibacterial agent (selected from imipenem, meropenem, ertapenem or doripenem) and a compound of Formula (I) may be present in the composition in their free forms or in the form of their pharmaceutically acceptable derivative (such as salts, pro-drugs, metabolites, esters, ethers, hydrates, polymorphs, solvates, complexes, or adducts). The specified ratio of carbapenem antibacterial agent (selected from imipenem, meropenem, ertapenem or doripenem) and compound of Formula (I) in the composition is calculated on the basis of their free forms.

Individual amounts of a compound of Formula (I) or a stereoisomer or a pharmaceutically acceptable derivative thereof, and a carbapenem antibacterial agent selected from imipenem, meropenem, ertapenem, doripenem or a pharmaceutically acceptable derivative thereof in the composition may vary depending on clinical requirements. In some embodiments, a compound of Formula (I), or a stereoisomer or a pharmaceutically acceptable derivative thereof in the composition is present in an amount from about 0.01 gram to about 10 gram. In some other embodiments, carbapenem antibacterial agent selected from imipenem, meropenem, ertapenem, doripenem or a pharmaceutically acceptable derivative thereof in the composition is present in an amount from about 0.01 gram to about 10 gram.

In some embodiments, the pharmaceutical composition according to the invention comprises about 0.25 gram of a compound of Formula (I), or a stereoisomer or a pharmaceutically acceptable derivative thereof, and about 0.5 gram of a carbapenem antibacterial agent selected from imipenem, meropenem, ertapenem, doripenem or a pharmaceutically acceptable derivative thereof.

In some other embodiments, the pharmaceutical composition according to the invention comprises about 0.5 gram of a compound of Formula (I), or a stereoisomer or a pharmaceutically acceptable derivative thereof, and about 0.5 gram of a carbapenem antibacterial agent selected from imipenem, meropenem, ertapenem, doripenem or a pharmaceutically acceptable derivative thereof.

In some embodiments, the pharmaceutical composition according to the invention comprises about 1 gram of a compound of Formula (I), or a stereoisomer or a pharmaceutically acceptable derivative thereof, and about 0.5 gram of a carbapenem antibacterial agent selected from imipenem, meropenem, ertapenem, doripenem or a pharmaceutically acceptable derivative thereof.

In some embodiments, the pharmaceutical composition according to the invention comprises about 0.25 gram of a compound of Formula (I), or a stereoisomer or a pharmaceutically acceptable derivative thereof, and about 1 gram of a carbapenem antibacterial agent selected from imipenem, meropenem, ertapenem, doripenem or a pharmaceutically acceptable derivative thereof.

In some embodiments, the pharmaceutical composition according to the invention comprises about 0.5 gram of a compound of Formula (I), or a stereoisomer or a pharmaceutically acceptable derivative thereof, and about 1 gram of a carbapenem antibacterial agent selected from imipenem, meropenem, ertapenem, doripenem or a pharmaceutically acceptable derivative thereof.

In some embodiments, the pharmaceutical composition according to the invention comprises about 1 gram of a compound of Formula (I), or a stereoisomer or a pharmaceutically acceptable derivative thereof, and about 1 gram of a carbapenem antibacterial agent selected from imipenem, meropenem, ertapenem, doripenem or a pharmaceutically acceptable derivative thereof.

In some embodiments, the pharmaceutical composition according to the invention comprises about 2 gram of a compound of Formula (I), or a stereoisomer or a pharmaceutically acceptable derivative thereof, and about 1 gram of a carbapenem antibacterial agent selected from imipenem, meropenem, ertapenem, doripenem or a pharmaceutically acceptable derivative thereof.

In some other embodiments, the pharmaceutical composition according to the invention comprises about 0.25 gram of a compound of Formula (I), or a stereoisomer or a pharmaceutically acceptable derivative thereof, and about 2 gram of a carbapenem antibacterial agent selected from imipenem, meropenem, ertapenem, doripenem or a pharmaceutically acceptable derivative thereof.

In some other embodiments, the pharmaceutical composition according to the invention comprises about 0.5 gram of a compound of Formula (I), or a stereoisomer or a pharmaceutically acceptable derivative thereof, and about 2 gram of a carbapenem antibacterial agent selected from imipenem, meropenem, ertapenem, doripenem or a pharmaceutically acceptable derivative thereof.

In some other embodiments, the pharmaceutical composition according to the invention comprises about 1 gram of a compound of Formula (I), or a stereoisomer or a pharmaceutically acceptable derivative thereof, and about 2 gram of a carbapenem antibacterial agent selected from imipenem, meropenem, ertapenem, doripenem or a pharmaceutically acceptable derivative thereof.

In some other embodiments, the pharmaceutical composition according to the invention comprises about 2 gram of a compound of Formula (I), or a stereoisomer or a pharmaceutically acceptable derivative thereof, and about 2 gram of a carbapenem antibacterial agent selected from imipenem, meropenem, ertapenem, doripenem or a pharmaceutically acceptable derivative thereof.

The pharmaceutical composition and methods according to the invention use active as well as inactive (or inert) ingredients. In some embodiments, there is provided a pharmaceutical composition comprising the active ingredients, said active ingredients consisting of: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof. The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatine, sucrose, magnesium carbonate, wetting agents, emulsifying agents, solubilizing agents, buffering agents, lubricants, preservatives, stabilizing agents, binding agents and the like.

The pharmaceutical compositions or the active ingredients according to the present invention may be formulated into a variety of dosage forms, such as solid, semi-solid, liquid and aerosol dosage forms. Typical, non-limiting examples of some dosage forms include tablets, capsules, powders, solutions, suspensions, suppositories, aerosols, granules, emulsions, syrups, elixirs and the like.

Depending on the requirement, the pharmaceutical compositions according to the invention may also be prepared and packaged in bulk form. Alternatively, the pharmaceutical compositions of the invention may be prepared and packaged in unit dosage form.

In some embodiments, pharmaceutical compositions according to the invention are in the form of a powder or a solution. In some other embodiments, pharmaceutical compositions according to the invention are present in the form of a powder or a solution that can be reconstituted by addition of a compatible reconstitution diluent prior to administration. In some other embodiments, pharmaceutical compositions according to the invention are in the form of a frozen composition that can be diluted with a compatible reconstitution diluent prior to administration. Typical, non-limiting example of suitable compatible reconstitution diluent includes water.

In some other embodiments, pharmaceutical compositions according to the invention are present in the form ready to use for oral or parenteral administration.

The compositions according to the invention can be formulated into various dosage forms wherein the active ingredients and/or excipients may be present either together (e.g. as an admixture) or as separate components. When the various ingredients in the composition are formulated as a mixture, such compositions can be delivered by administering such a mixture to a subject using any suitable route of administration. Alternatively, pharmaceutical compositions according to the invention may also be formulated into a dosage form wherein one or more ingredients (such as active or inactive ingredients) are present as separate components. The composition or dosage form wherein the ingredients do not come as a mixture, but come as separate components, such composition/dosage form may be administered in several ways. In one possible way, the ingredients may be mixed in the desired proportions and the mixture is reconstituted in suitable reconstitution diluent and is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

In some embodiments, pharmaceutical compositions according to the invention are formulated into a dosage form such that a compound of Formula (I), or a stereoisomer or a pharmaceutically acceptable derivative thereof, and a carbapenem antibacterial agent selected from imipenem, meropenem, ertapenem, doripenem or a pharmaceutically acceptable derivative thereof, are present in the composition as admixture or as a separate components. In some other embodiments, pharmaceutical compositions according to the invention are formulated into a dosage form such that a compound of Formula (I) or a stereoisomer or a pharmaceutically acceptable derivative thereof, and carbapenem antibacterial agent selected from imipenem, meropenem, ertapenem, doripenem or a pharmaceutically acceptable derivative thereof, are present in the composition as separate components.

In one general aspect, pharmaceutical compositions according to the invention are used in treatment or prevention of a bacterial infection.

In another general aspect, there are provided methods for treating or preventing a bacterial infection in a subject, said method comprising administering to said subject effective amount of a pharmaceutical composition according to the invention. In case of dosage forms wherein a compound of Formula (I), or a stereoisomer or a pharmaceutically acceptable derivative thereof, and carbapenem antibacterial agent selected from imipenem, meropenem, ertapenem, doripenem or a pharmaceutically acceptable derivative thereof, are present in the composition as separate components; a compound of Formula (I), or a stereoisomer or a pharmaceutically acceptable derivative thereof may be administered before, after or simultaneously with the administration of a carbapenem antibacterial agent selected from imipenem, meropenem, ertapenem, doripenem or a pharmaceutically acceptable derivative thereof. In some embodiments, the compositions according to the invention are administered orally or parenterally.

In yet another general aspect, there are provided methods for treating or preventing bacterial infections in a subject, said methods comprising administering to said subject an effective amount of: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof:

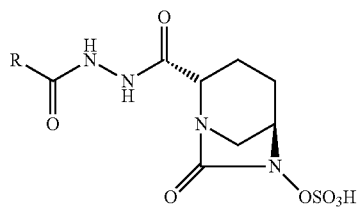

Formula (I)

wherein, R is heterocycloalkyl.

In another general aspect, there are provided methods for treating or preventing bacterial infections in a subject, said methods comprising administering to said subject an effective amount of: (a) a carbapenem antibacterial agent selected from imipenem, meropenem, ertapenem, doripenem or a pharmaceutically acceptable derivative thereof, and (b) a compound of Formula (I) or a stereoisomer or a pharmaceutically acceptable derivative thereof; wherein amount of a compound of Formula (I), or a stereoisomer or a pharmaceutically acceptable derivative thereof administered is from about 0.25 gram to about 4 gram per gram of the carbapenem antibacterial agent selected from imipenem, meropenem, ertapenem, doripenem or a pharmaceutically acceptable derivative thereof.

In some embodiments, there is provided a method for treating or preventing a bacterial infection in a subject, said method comprising administering to said subject: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof, in any of the following amounts:

(i) about 0.25 gram of a compound of Formula (I), or a stereoisomer or a pharmaceutically acceptable derivative thereof, and about 0.5 gram of the carbapenem antibacterial agent selected from imipenem, meropenem, ertapenem, doripenem or a pharmaceutically acceptable derivative thereof;

(ii) about 0.5 gram of a compound of Formula (I), or a stereoisomer or a pharmaceutically acceptable derivative thereof, and about 0.5 gram of the carbapenem antibacterial agent selected from imipenem, meropenem, ertapenem, doripenem or a pharmaceutically acceptable derivative thereof;

(iii) about 1 gram of a compound of Formula (I), or a stereoisomer or a pharmaceutically acceptable derivative thereof, and about 0.5 gram of the carbapenem antibacterial agent selected from imipenem, meropenem, ertapenem, doripenem or a pharmaceutically acceptable derivative thereof;

(iv) about 0.25 gram of a compound of Formula (I), or a stereoisomer or a pharmaceutically acceptable derivative thereof, and about 1 gram of the carbapenem antibacterial agent selected from imipenem, meropenem, ertapenem, doripenem or a pharmaceutically acceptable derivative thereof;

(v) about 0.5 gram of a compound of Formula (I), or a stereoisomer or a pharmaceutically acceptable derivative thereof, and about 1 gram of the carbapenem antibacterial agent selected from imipenem, meropenem, ertapenem, doripenem or a pharmaceutically acceptable derivative thereof;

(vi) about 1 gram of a compound of Formula (I), or a stereoisomer or a pharmaceutically acceptable derivative thereof, and about 1 gram of the carbapenem antibacterial agent selected from imipenem, meropenem, ertapenem, doripenem or a pharmaceutically acceptable derivative thereof;

(vii) about 2 gram of a compound of Formula (I), or a stereoisomer or a pharmaceutically acceptable derivative thereof, and about 1 gram of the carbapenem antibacterial agent selected from imipenem, meropenem, ertapenem, doripenem or a pharmaceutically acceptable derivative thereof;

(viii) about 0.25 gram of a compound of Formula (I), or a stereoisomer or a pharmaceutically acceptable derivative thereof, and about 2 gram of the carbapenem antibacterial agent selected from imipenem, meropenem, ertapenem, doripenem or a pharmaceutically acceptable derivative thereof;

(ix) about 0.5 gram of a compound of Formula (I), or a stereoisomer or a pharmaceutically acceptable derivative thereof, and about 2 gram of the carbapenem antibacterial agent selected from imipenem, meropenem, ertapenem, doripenem or a pharmaceutically acceptable derivative thereof;

(x) about 1 gram of a compound of Formula (I), or a stereoisomer or a pharmaceutically acceptable derivative thereof, and about 2 gram of the carbapenem antibacterial agent selected from imipenem, meropenem, ertapenem, doripenem or a pharmaceutically acceptable derivative thereof;

(xi) about 2 gram of a compound of Formula (I), or a stereoisomer or a pharmaceutically acceptable derivative thereof, and about 2 gram of the carbapenem antibacterial agent selected from imipenem, meropenem, ertapenem, doripenem or a pharmaceutically acceptable derivative thereof;

In some embodiments, in the methods according to the invention, a compound of Formula (I), or a stereoisomer or a pharmaceutically acceptable derivative thereof is administered in an amount from about 0.01 gram to about 10 gram. In some other embodiments, in the methods according to the invention, a carbapenem antibacterial agent selected from imipenem, meropenem, ertapenem, doripenem or a pharmaceutically acceptable derivative thereof is administered in an amount from about 0.01 gram to about 10 gram.

In some embodiments, in the methods according to the invention, a compound of Formula (I), or a stereoisomer or a pharmaceutically acceptable derivative thereof is administered before, after or simultaneously with the administration of a carbapenem antibacterial agent selected from imipenem, meropenem, ertapenem, doripenem or a pharmaceutically acceptable derivative thereof.

In some embodiments, the compound of Formula (I), or a stereoisomer or a pharmaceutically acceptable derivative thereof, and the carbapenem antibacterial agent selected from imipenem, meropenem, ertapenem, doripenem or a pharmaceutically acceptable derivative thereof, are administered orally or parenterally.

In the methods according to the invention, the pharmaceutical composition and/or other pharmaceutically active ingredients disclosed herein may be administered by any appropriate method, which serves to deliver the composition, or its constituents, or the active ingredients to the desired site. The method of administration can vary depending on various factors, such as for example, the components of the pharmaceutical composition and the nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, the compositions or one or more active ingredients according to the invention are administered parenterally or orally.

In some embodiments, there is provided a method for increasing antibacterial effectiveness of a carbapenem antibacterial agent selected from imipenem, meropenem, ertapenem, doripenem or a pharmaceutically acceptable derivative thereof, in a subject, said method comprising co-administering the said carbapenem antibacterial agent selected from imipenem, meropenem, ertapenem, doripenem or a pharmaceutically acceptable derivative thereof, with a compound of Formula (I), or a stereoisomer or a pharmaceutically acceptable derivative thereof. In some other embodiments, there is provided a method for increasing antibacterial effectiveness of a carbapenem antibacterial agent selected from imipenem, meropenem, ertapenem, doripenem or a pharmaceutically acceptable derivative thereof in a subject, said method comprising co-administering the said carbapenem antibacterial agent selected from imipenem, meropenem, ertapenem, doripenem or a pharmaceutically acceptable derivative thereof, with a compound of Formula (I), or a stereoisomer or a pharmaceutically acceptable derivative thereof, wherein the amount of a compound of Formula (I), or a stereoisomer or a pharmaceutically acceptable derivative thereof administered is from about 0.25 gram to about 4 gram per gram of the carbapenem antibacterial agent selected from imipenem, meropenem, ertapenem, doripenem or a pharmaceutically acceptable derivative thereof.

In general, imipenem is known to be susceptible to degradation by a renal enzyme known as dehydropeptidase (DHP), which may reduce overall availability of imipenem and reduce the efficacy of the treatment. One way to minimize degradation of imipenem by dehydropeptidase is to co-administer imipenem with a suitable dehydropeptidase inhibitor (DHP inhibitor). Typical, non-limiting example of a suitable dehydropeptidase inhibitor includes cilastatin or a pharmaceutically acceptable derivative thereof. In some embodiments, the pharmaceutical compositions and methods according to invention comprise use of a suitable dehydropeptidase inhibitor. When used in compositions, the dehydropeptidase inhibitor may be present in the composition in admixture with one or more ingredients or as a separate component. When used in methods according to the invention, the dehydropeptidase inhibitor may be administered together with the composition or given separate from the composition (or its components).

In some embodiments, pharmaceutical compositions according to the invention further comprise a dehydropeptidase inhibitor. In some other embodiments, pharmaceutical compositions according to the invention comprise a dehydropeptidase inhibitor, which is cilastatin or a pharmaceutically acceptable derivative thereof. In some embodiments, the methods according to the invention further comprise administration of a dehydropeptidase inhibitor. In some other embodiments, the methods according to the invention comprise administration of a dehydropeptidase inhibitor, which is cilastatin or a pharmaceutically acceptable derivative thereof.

The amount of a dehydropeptidase inhibitor that can be used in the compositions or methods according to the invention depends on the therapeutic effect desired. In some embodiments, the dehydropeptidase inhibitor is used in an amount which is about 0.1 to about 10 gram per gram of imipenem. In some other embodiments, the weight ratio of dehydropeptidase inhibitor to imipenem used in the pharmaceutical compositions and methods according to the invention is about 1:1.

A wide variety of bacterial infections can be treated or prevented using compositions and methods according to the invention. Typical, non-limiting examples of bacterial infections that can be treated or prevented using methods and/or pharmaceutical compositions according to the invention include *E. coli* infections, *Yersinia pestis* (pneumonic plague), staphylococcal infection, mycobacteria infection, bacterial pneumonia, *Shigella* dysentery, *Serratia* infections, *Candida* infections, *Cryptococcal* infection, anthrax, tuberculosis or infections caused by *Pseudomonas aeruginosa*, *Acinetobacter baumannii* or methicillin resistant *Staphylococcus aurues* (MRSA) etc.

The pharmaceutical compositions and methods according to the invention are useful in treatment or prevention of several infections, including for example, skin and soft tissue infections, febrile neutropenia, urinary tract infection, intraabdominal infections, respiratory tract infections, pneumonia (nosocomial), bacteremia meningitis, surgical infections and the like.

In some embodiments, pharmaceutical compositions and methods according to the invention are used in treatment or prevention of infections caused by resistant bacteria. In some other embodiments, the compositions and methods according to the invention are used in treatment or prevention of infections caused by bacteria producing one or more beta-lactamase enzymes. In some other embodiments, the compositions and methods according to the invention are used in treatment or prevention of infections caused by bacteria producing one or more extended spectrum beta-lactamase enzymes.

In some embodiments, there is provided a method for preventing or treating a bacterial infection in a subject, said infection being caused by bacteria producing carbapenem-hydrolyzing beta-lactamases, said method comprising administering to said subject: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof.

In some embodiments, there is provided a method for preventing or treating a bacterial infection in a subject, said infection being caused by bacteria producing metallo beta-lactamase enzymes, said method comprising administering to said subject: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof.

In some embodiments, there is provided a method for preventing or treating a bacterial infection in a subject, said infection being caused by bacteria harboring resistance due to AmpC beta-lactamase enzymes or OprD channels or efflux pumps, said methods comprising administering to said subject: (a) a carbapenem antibacterial agent selected from imipenem, meropenem, ertapenem, doripenem or a pharmaceutically acceptable derivative thereof, and (b) a compound of Formula (I), or a stereoisomer or a pharmaceutically acceptable derivative thereof.

In general, the pharmaceutical compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, Escherichia coli, Pseudomonas aeruginosa, Staphylococcus aureus, Enterobacter, Klebsiella, Citrobacter* and a like.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

The antibacterial activity of combinations according to the invention against resistant bacterial strains was investigated. Minimum Inhibitory Concentration (MIC) determination for the combinations according to invention was carried out in Muller Hinton Agar (MHA) (BD, USA) according to Clinical and Laboratory Standards Institute (CLSI) recommendations, (Clinical and Laboratory Standards Institute (CLSI), Performance Standards for Antimicrobial Susceptibility Testing, $20^{th}$ Informational Supplement, M 100-S20, Volume 30, No. 1, 2010). In short, the test strains were adjusted to deliver about $10^4$ CFU per spot with a multipoint inoculator (Applied Quality Services, UK). The plates were pored with MHA containing doubling concentration range of the test combinations according to invention. The plates were inoculated and were incubated at 35° C. for 18 hours. MICs were read as the lowest concentration of drug that completely inhibited bacterial growth.

The synergistic killing effect of the combinations according to invention was studied by performing time kill studies. In a typical time kill study, the freshly grown cultures were diluted to the required cell density (initial starting inoculum) in Cation adjusted Muller Hinton broth medium (BD, USA). The antibacterial agents (either alone or in combination) at the required concentrations were added into the culture-containing medium. The samples were incubated under shaking condition (120 rpm) at 37° C. Enumeration of viable bacterial count was done every 2 hour by diluting in normal saline and plating on to the Tryptic Soya Agar plates (BD, USA). The plates were incubated for 24 hours to arrive at the viable bacterial count. The results are expressed in terms of $Log_{10}$ CFU per ml. In general, the decrease of 1 $Log_{10}$ CFU/ml, corresponds to 90% killing of bacteria. Similarly, 2 $Log_{10}$ CFU/ml reductions indicates to 99% killing of bacteria and 3 $Log_{10}$ CFU/ml reductions is equal to 99.9% killing of bacteria.

The following two compounds represented by a general Formula (I) were used in studies:
1. trans-sulfuric acid mono-[2-(N'-[(R)-piperidin-3-carbonyl]-hydrazinocarbonyl)-7-oxo-1,6-diaza-bicyclo[3.2.1]oct-6-yl] ester (Compound A)

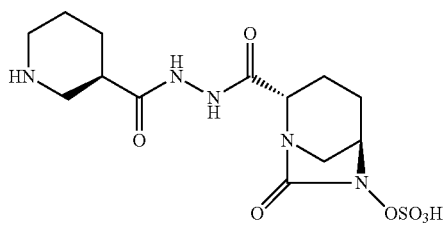

2. trans-sulfuric acid mono-[2-(N'-[(R)-pyrrolidin-3-carbonyl]-hydrazinocarbonyl)-7-oxo-1,6-diaza-bicyclo[3.2.1]oct-6-yl] ester (Compound B)

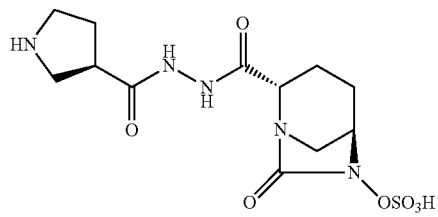

Example 1

The results on antibacterial activity of a carbapenem antibacterial agent selected from imipenem, meropenem, ertapenem and doripenem alone and in combination with Compound A or Compound B, against highly resistant strains of *Pseudomonas aeruginosa* are given in Table 1. The strains of *P. aeruginosa* selected for study confer resistance due to either increased AmpC expression or upregulated efflux pumps or reduced expression of OprD. For example, *P. aeruginosa* 2779 harbors resistance due to increased AmpC expression (300 times) and increased efflux; *P. aeruginosa* 1405 harbors resistance due to increased AmpC expression (600 times), reduced OprD expression and increased efflux; *P. aeruginosa* R 70 harbors resistance due to reduced OprD expression and increased efflux; and *P. aeruginosa* J 154 harbors resistance due to reduced OprD. As can be seen from the data, imipenem, meropenem, ertapenem, doripenem, Compound A and Compound B, when used alone, exhibited higher MIC values. However, surprisingly, it has been found that MIC values of imipenem, meropenem, ertapenem and doripenem decreased significantly in presence of Compound A or Compound B (representative compounds of Formula (I)). The lower MIC values suggest that the combinations according to the invention exhibited good antibacterial activity against highly resistant strains of *P. aeruginosa*.

Example 2

The results on the antibacterial activity of a combination comprising a carbapenem antibacterial agent selected from imipenem, meropenem, ertapenem and doripenem alone or in combination with a Compound A, against *P. aeruginosa* 1405 are given in Table 2. *P. aeruginosa* 1405 harboring triple resistance mechanism (increased AmpC expression (600 times), reduced OprD expression and increased efflux). As can be seen from the data in the Table 2, imipenem, meropenem, ertapenem and doripenem and Compound A, when used alone, failed to reduce the bacterial counts through out the duration of the study. However, surprisingly, it has been observed that combination of a carbapenem antibacterial agent selected from imipenem, meropenem, ertapenem or doripenem, and Compound A reduced the bacterial counts significantly through out the duration of the study. Thus, it appears from the data of Table 2, that combinations of according to invention exhibited synergistic antibacterial activity.

Example 3

The results on antibacterial activity of a combination comprising a carbapenem antibacterial agent selected from imipenem, meropenem, ertapenem or doripenem, and Compound B against *P. aeruginosa* 1405 harboring triple resistance mechanism (increased AmpC expression (600 times), reduced OprD expression and increased efflux) are given in Table 3. As can be seen from the data in the Table 3; imipenem, meropenem, ertapenem, doripenem and Compound B, when used alone, failed to reduce the bacterial counts through out the duration of the study. However, surprisingly, it has been observed that combination of a carbapenem antibacterial agent selected from imipenem, meropenem, ertapenem or doripenem, and Compound B reduced the bacterial counts significantly through out the duration of the study. Thus, combinations according to invention exhibited synergistic antibacterial activity against highly resistant *P. aeruginosa* 1405.

TABLE 1

Antibacterial activity of a carbapenem antibacterial agent selected from imipenem, meropenem, ertapenem and doripenem, alone and in combination with Compound A or Compound B, against highly resistant strains of *Pseudomonas aeruginosa*.

| | | | | | | | | MIC (mcg/ml) of [IPM] in presence of | |
|---|---|---|---|---|---|---|---|---|---|
| | Strain | | MIC (mcg/ml) | | | | | | |
| Sr. | [Resistance Mechanism] | [IPM] | [MEM] | [ERT] | [DOR] | [A] at 4 mcg/ml | [B] at 4 mcg/ml | [A] at 4 mcg/ml | [B] at 4 mcg/ml |
| 1. | *P. aeruginosa* 2779 [AmpC (300 times expression) + increased efflux] | 1 | 1 | 32 | 0.5 | 16 | 8 | ≤0.25 | 0.12 |

TABLE 1-continued

Antibacterial activity of a carbapenem antibacterial agent selected from imipenem, meropenem, ertapenem and doripenem, alone and in combination with Compound A or Compound B, against highly resistant strains of *Pseudomonas aeruginosa*.

| Sr. | Strain [Resistance Mechanism] | | | | | | | |
|---|---|---|---|---|---|---|---|---|
| 2. | *P. aeruginosa* 1405 [Amp C (600 times) + reduced OprD expression + increased efflux] | 8 | 8 | >128 | 8 | 8 | 8 | 1 | 1 |
| 3. | *P. aeruginosa* R 70 [Reduced OprD + increased efflux] | 8 | >32 | >128 | 16 | 8 | 2 | 2 | ≤0.12 |
| 4. | *P. aeruginosa* J 154 [Reduced OprD] | 16 | 16 | >128 | 8 | 16 | 8 | 4 | 0.5 |

| | Strain [Resistance Mechanism] | MIC (mcg/ml) of [MEM] in presence of | | MIC (mcg/ml) of [ERT] in presence of | | MIC (mcg/ml) of [DOR] in presence of | |
|---|---|---|---|---|---|---|---|
| Sr. | | [A] at 4 mcg/ml | [B] at 4 mcg/ml | [A] at 4 mcg/ml | [B] at 4 mcg/ml | [A] at 4 mcg/ml | [B] at 4 mcg/ml |
| 1. | *P. aeruginosa* 2779 [AmpC (300 times expression) + increased efflux] | 0.12 | 0.12 | 4 | 4 | 0.12 | 0.06 |
| 2. | *P. aeruginosa* 1405 [Amp C (600 times) + reduced OprD expression + increased efflux] | 4 | 0.12 | 128 | 64 | 4 | 4 |
| 3. | *P. aeruginosa* R 70 [Reduced OprD + increased efflux] | 16 | ≤0.12 | >128 | ≤0.12 | 8 | <0.12 |
| 4. | *P. aeruginosa* J 154 [Reduced OprD] | 8 | <0.25 | >128 | 128 | 8 | 4 |

Note:
[IPM] stands for imipenem; [MEM] stands for meropenem; [ERT] stands for ertapenem; [DOR] stands for doripenem; [A] stands for compound A; and [B] stands for compound B.

TABLE 2

Antibacterial activity of combination comprising a carbapenem antibacterial agent selected from imipenem, meropenem, ertapenem or doripenem, and Compound A against *Pseudomonas aeruginosa* 1405.

| Sr. | Combination | Bacterial count ($Log_{10}$ CFU/ml) | | | |
|---|---|---|---|---|---|
| | | 0 hour | 2 hour | 4 hour | 6 hour |
| 1. | Control (No active ingredient) | 6.84 | 7.07 | 7.9 | 8.54 |
| 2. | Imipenem (4 mcg/ml) | 6.84 | 6.39 | 7.04 | 8.16 |
| 3. | Meropenem (4 mcg/ml) | 6.84 | 5.95 | 6.89 | 7.02 |
| 4. | Ertapenem (16 mcg/ml) | 6.84 | 6.90 | 7.87 | 7.65 |
| 5. | Doripenem (4 mcg/ml) | 6.84 | 6.17 | 5.90 | 6.60 |
| 6. | Compound A (4 mcg/ml) | 6.84 | 6.81 | 7.84 | 8.06 |
| 7. | Compound A (8 mcg/ml) | 6.84 | 6.48 | 7.4 | 7.54 |
| 8. | Imipenem (4 mcg/ml) + Compound A (4 mcg/ml) | 6.84 | 4.69 | 4.17 | 4.16 |
| 9. | Imipenem (4 mcg/ml) + Compound A (8 mcg/ml) | 6.84 | 4.6 | 4.06 | 3.54 |
| 10. | Meropenem (4 mcg/ml) + Compound A (4 mcg/ml) | 6.84 | 5.81 | 4.9 | 4.65 |
| 11. | Meropenem (4 mcg/ml) + Compound A (8 mcg/ml) | 6.84 | 5.6 | 4 | 3.5 |
| 12. | Ertapenem (16 mcg/ml) + Compound A (4 mcg/ml) | 6.84 | 6.47 | 6.41 | 6.77 |
| 13. | Ertapenem (16 mcg/ml) + Compound A (8 mcg/ml) | 6.84 | 5.65 | 5.77 | 5.84 |
| 14. | Doripenem (4 mcg/ml) + Compound A (4 mcg/ml) | 6.84 | 5.60 | 4.65 | 4.65 |

Example 4

The results on the antibacterial activity of imipenem, meropenem, ertapenem and doripenem alone or in combination with Compound A against *Pseudomonas aeruginosa* R70 are given in Table 4. *P. aeruginosa* R70 harbors double resistance mechanism (reduced OprD expression and increased efflux). As can be seen from the data in the Table 4, imipenem, meropenem, ertapenem, doripenem and Compound A, when used alone, failed to reduce the bacterial counts through out the duration of the study. However, surprisingly, it has been observed that combination of a carbapenem antibacterial agent selected from imipenem, meropenem, ertapenem or doripenem, and Compound A reduced the bacterial counts through out the duration of the study. As can be seen from the data, combinations according to invention reduced the bacterial count of *P. aeruginosa* R70 significantly and exhibited synergistic antibacterial activity.

Example 5

The results on antibacterial activity of combination comprising a carbapenem antibacterial agent selected from imipenem, meropenem, ertapenem or doripenem, and Compound B against *Pseudomonas aeruginosa* R70, harboring double resistance mechanism (reduced OprD expression and increased efflux) are given in Table 5. As can be seen from the data, imipenem, meropenem, ertapenem, doripenem, and Compound B, when used alone, failed to reduce the bacterial counts through out the duration of the study. However, surprisingly, it has been observed that combinations according to invention significantly reduced the bacterial counts through out the duration of the study and hence, exhibited good synergistic antibacterial activity.

TABLE 3

Antibacterial activity of a combination comprising a carbapenem antibacterial agent selected from imipenem, meropenem, ertapenem or doripenem, and Compound B against *Pseudomonas aeruginosa* 1405.

| | | Bacterial count ($Log_{10}$ CFU/ml) | | | |
|---|---|---|---|---|---|
| Sr. | Combination | 0 hour | 2 hour | 4 hour | 6 hour |
| 1. | Control (No active ingredient) | 6.81 | 6.4 | 7.85 | 8.18 |
| 2. | Imipenem (4 mcg/ml) | 6.81 | 6.4 | 7.78 | 7.93 |
| 3. | Meropenem (4 mcg/ml) | 6.81 | 6.8 | 7.0 | 7.3 |
| 4. | Ertapenem (16 mcg/ml) | 6.81 | 6.90 | 7.87 | 7.65 |
| 5. | Doripenem (4 mcg/ml) | 6.81 | 6.17 | 5.90 | 6.60 |
| 6. | Compound B (2 mcg/ml) | 6.81 | 6.48 | 7.6 | 7.5 |
| 7. | Compound B (4 mcg/ml) | 6.81 | 6.54 | 6.65 | 6.7 |
| 8. | Imipenem (4 mcg/ml) + Compound B (2 mcg/ml) | 6.81 | 4.38 | 3.88 | 4.0 |
| 9. | Imipenem (4 mcg/ml) + Compound B (4 mcg/ml) | 6.81 | 4.2 | 3.8 | 3.3 |
| 10. | Meropenem (4 mcg/ml) + Compound B (2 mcg/ml) | 6.81 | 5.3 | 4.0 | 4 |
| 11. | Meropenem (4 mcg/ml) + Compound B (4 mcg/ml) | 6.81 | 4.48 | 3.4 | 3.32 |
| 12. | Ertapenem (16 mcg/ml) + Compound B (2 mcg/ml) | 6.81 | 6.33 | 6.14 | 6.77 |
| 13. | Ertapenem (4 mcg/ml) + Compound B (4 mcg/ml) | 6.81 | 5.60 | 5.27 | 5 |
| 14. | Doripenem (4 mcg/ml) + Compound B (4 mcg/ml) | 6.81 | 4.20 | 4.39 | 3.90 |

The results given in the Tables 1-5, clearly and surprisingly demonstrate the potent antibacterial activity of the combinations according to the present invention against highly resistant bacterial strains. Imipenem, meropenem, ertapenem, doripenem and representative compounds of Formula (I) (Compound A or Compound B) when used alone, did not exhibit significant antibacterial activity. However, surprisingly the combinations according to invention exhibited unusual and unexpected synergistic antibacterial effect against highly resistant bacterial strains. Thus, combination of a carbapenem antibacterial agent selected from imipenem, meropenem, ertapenem or doripenem, and a compound of Formula (I) has tremendous beneficial effect in inhibiting highly resistant bacterial strains demonstrating the noteworthy therapeutic advance in the treatment of infections caused by resistant bacteria.

TABLE 4

Antibacterial activity of a combination comprising a carbapenem antibacterial agent selected from imipenem, meropenem, ertapenem or doripenem, and Compound A against *Pseudomonas aeruginosa* R70.

| | | Bacterial count ($Log_{10}$ CFU/ml) | | | |
|---|---|---|---|---|---|
| Sr. | Combination | 0 hour | 2 hour | 4 hour | 6 hour |
| 1. | Control (No active ingredient) | 6.62 | 7.34 | 8.25 | 8.48 |
| 2. | Imipenem (2 mcg/ml) | 6.62 | 5.7 | 5.98 | 6.78 |
| 3. | Meropenem (4 mcg/ml) | 6.62 | 7.07 | 6.84 | 8.36 |
| 4. | Ertapenem (16 mcg/ml) | 6.62 | 6.87 | 7.47 | 8.16 |
| 5. | Doripenem (4 mcg/ml) | 6.62 | 5.74 | 5.65 | 5.65 |
| 6. | Compound A (4 mcg/ml) | 6.62 | 7.07 | 8.35 | 8.48 |
| 7. | Compound A (8 mcg/ml) | 6.62 | 6.9 | 7.11 | 7.16 |
| 8. | Imipenem (2 mcg/ml) + Compound A (4 mcg/ml) | 6.62 | 5.26 | 4.95 | 4.1 |
| 9. | Imipenem (2 mcg/ml) + Compound A (8 mcg/ml) | 6.62 | 4.78 | 4.6 | 3.8 |
| 10. | Meropenem (4 mcg/ml) + Compound A (4 mcg/ml) | 6.62 | 5.44 | 5.7 | 6.7 |
| 11. | Meropenem (4 mcg/ml) + Compound A (8 mcg/ml) | 6.62 | 5.34 | 5.78 | 5.48 |
| 12. | Ertapenem (16 mcg/ml) + Compound A (4 mcg/ml) | 6.62 | 6.81 | 7.41 | 7.33 |
| 13. | Ertapenem (16 mcg/ml) + Compound A (8 mcg/ml) | 6.62 | 6.57 | 6.90 | 6.16 |
| 14. | Doripenem (4 mcg/ml) + Compound A (4 mcg/ml) | 6.62 | 5.77 | 5.25 | 5.34 |

TABLE 5

Antibacterial activity of a combination comprising a carbapenem antibacterial agent selected from imipenem, meropenem, ertapenem or doripenem, and Compound B against *Pseudomonas aeruginosa* R70.

| | | Bacterial count ($Log_{10}$ CFU/ml) | | | |
|---|---|---|---|---|---|
| Sr. | Combination | 0 hour | 2 hour | 4 hour | 6 hour |
| 1. | Control (No active ingredient) | 6.44 | 6.3 | 8.2 | 8.23 |
| 2. | Imipenem (2 mcg/ml) | 6.44 | 5.6 | 5.8 | 6.3 |
| 3. | Meropenem (4 mcg/ml) | 6.44 | 6.14 | 7.07 | 7.3 |
| 4. | Ertapenem (16 mcg/ml) | 6.44 | 6.46 | 7.17 | 7.13 |
| 5. | Doripenem (4 mcg/ml) | 6.44 | 5.74 | 5.65 | 5.65 |
| 6. | Compound B (2 mcg/ml) | 6.44 | 7.11 | 7.3 | 7.6 |
| 7. | Compound B (4 mcg/ml) | 6.44 | 6.2 | 6.4 | 6.0 |
| 8. | Imipenem (2 mcg/ml) + Compound B (2 mcg/ml) | 6.44 | 4.8 | 4.5 | 4.3 |
| 9. | Imipenem (2 mcg/ml) + Compound B (4 mcg/ml) | 6.44 | 4.7 | 4.5 | 4.2 |
| 10. | Meropenem (4 mcg/ml) + Compound B (2 mcg/ml) | 6.44 | 5.1 | 5.2 | 4.6 |
| 11. | Meropenem (4 mcg/ml) + Compound B (4 mcg/ml) | 6.44 | 5.3 | 5.0 | 4.2 |
| 12. | Ertapenem(16 mcg/ml) + Compound B (2 mcg/ml) | 6.44 | 6.46 | 7.17 | 7.13 |
| 13. | Ertapenem (16 mcg/ml) + Compound B (4 mcg/ml) | 6.44 | 6.17 | 5.74 | 5.60 |
| 14. | Doripenem (4 mcg/ml) + Compound B (4 mcg/ml) | 6.44 | 5.69 | 5.20 | 5.21 |

The invention claimed is:
1. A pharmaceutical composition comprising: (a) ertapenem, or a pharmaceutically acceptable salt thereof, and (b) a compound of Formula (I):

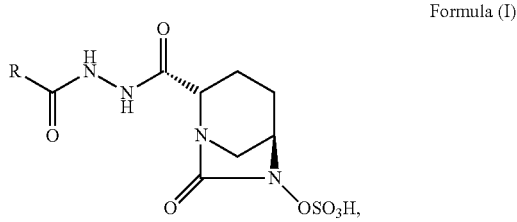

Formula (I)

or a stereoisomer or a pharmaceutically acceptable salt thereof, wherein R is piperidine or pyrrolidine.

2. The pharmaceutical composition according to claim 1, wherein the compound of Formula (I), or stereoisomer or pharmaceutically acceptable salt thereof is present in the composition in an amount from about 0.25 gram to about 4 grams per gram of the ertapenem, or pharmaceutically acceptable salt thereof.

3. The pharmaceutical composition according to claim 1, wherein the compound of Formula (I), or stereoisomer or pharmaceutically acceptable salt thereof is present in the composition in an amount from about 0.01 gram to about 10 grams.

4. The pharmaceutical composition according to claim 1, wherein the ertapenem, or pharmaceutically acceptable salt thereof is present in the composition in an amount from about 0.01 gram to about 10 grams.

5. The pharmaceutical composition according to claim 1, comprising: (a) the ertapenem, or pharmaceutically acceptable salt thereof, and (b) the compound of Formula (I), or stereoisomer or pharmaceutically acceptable salt thereof, in any one of following amounts:

(i) about 0.25 gram of the compound of Formula (I), or stereoisomer or pharmaceutically acceptable salt thereof, and about 0.5 gram of the ertapenem, or pharmaceutically acceptable salt thereof;

(ii) about 0.5 gram of the compound of Formula (I), or stereoisomer or pharmaceutically acceptable salt thereof, and about 0.5 gram of the ertapenem, or pharmaceutically acceptable salt thereof;

(iii) about 1 gram of the compound of Formula (I), or stereoisomer or pharmaceutically acceptable salt thereof, and about 0.5 gram of the ertapenem, or pharmaceutically acceptable salt thereof;

(iv) about 0.25 gram of the compound of Formula (I), or stereoisomer or pharmaceutically acceptable salt thereof, and about 1 gram of the ertapenem, or pharmaceutically acceptable salt thereof;

(v) about 0.5 gram of the compound of Formula (I), or stereoisomer or pharmaceutically acceptable salt thereof, and about 1 gram of the ertapenem, or pharmaceutically acceptable salt thereof;

(vi) about 1 gram of the compound of Formula (I), or stereoisomer or pharmaceutically acceptable salt thereof, and about 1 gram of the ertapenem, or pharmaceutically acceptable salt thereof;

(vii) about 2 grams of the compound of Formula (I), or stereoisomer or pharmaceutically acceptable salt thereof, and about 1 gram of the ertapenem, or pharmaceutically acceptable salt thereof;

(viii) about 0.25 gram of the compound of Formula (I), or stereoisomer or pharmaceutically acceptable salt thereof, and about 2 grams of the ertapenem, or pharmaceutically acceptable derivative salt thereof;

(ix) about 0.5 gram of the compound of Formula (I), or stereoisomer or pharmaceutically acceptable salt thereof, and about 2 grams of the ertapenem, or pharmaceutically acceptable salt thereof;

(x) about 1 gram of the compound of Formula (I), or stereoisomer or pharmaceutically acceptable salt thereof, and about 2 grams of the ertapenem, or pharmaceutically acceptable salt thereof; or (xi) about 2 grams of the compound of Formula (I), or stereoisomer or pharmaceutically acceptable salt thereof, and about 2 grams of the ertapenem, or pharmaceutically acceptable salt thereof.

6. The pharmaceutical composition according to claim 1, wherein the compound of Formula (I) is:

(a) trans-sulfuric acid mono-[2-(N'-[(R)-pyrrolidin-3-carbonyl]-hydrazinocarbonyl)-7-oxo-1,6-diaza-bicyclo[3.2.1]oct-6-yl] ester;

(b) (2S,5R) sulfuric acid mono-[2-(N'-[(R)-pyrrolidin-3-carbonyl]-hydrazinocarbonyl)-7-oxo-1,6-diaza-bicyclo[3.2.1]oct-6-yl] ester;

(f) trans-sulphuric acid mono-[2-(N'-[(R)-piperidin-3-carbonyl]-hydrazinocarbonyl)-7-oxo-1,6-diaza-bicyclo[3.2.1]oct-6-yl] ester;

(g) (2S,5R)-sulphuric acid mono-[2-(N'-[(R)-piperidin-3-carbonyl]-hydrazinocarbonyl)-7-oxo-1,6-diaza-bicyclo[3.2.1]oct-6-yl] ester;

or a stereoisomer or a pharmaceutically acceptable salt thereof.

7. The pharmaceutical composition according to claim 1, wherein the composition is formulated into a dosage form such that the compound of Formula (I), or stereoisomer or pharmaceutically acceptable salt thereof, and the ertapenem, or pharmaceutically acceptable salt thereof, are present in the composition as admixture or as separate components.

8. The pharmaceutical composition according to claim 7, wherein the compound of Formula (I), or stereoisomer or pharmaceutically acceptable salt thereof, and the ertapenem, or pharmaceutically acceptable salt thereof, are present in the composition as separate components.

9. The pharmaceutical composition according to claim 1, wherein the composition is in form of a powder or a solution.

10. The pharmaceutical composition according to claim 9, wherein the powder or solution can be reconstituted by addition of a compatible reconstitution diluent for use in parenteral or oral administration.

11. The pharmaceutical composition according to claim 1, wherein the compound of Formula (I) is (2S,5R)-sulphuric acid mono-[2-(N'-[(R)-piperidin-3-carbonyl]-hydrazinocarbonyl)-7-oxo-1,6-diaza-bicyclo[3.2.1]oct-6-yl] ester, or stereoisomer or pharmaceutically acceptable salt thereof.

12. The pharmaceutical composition according to claim 1, wherein the compound of Formula (I) is (2S,5R) sulfuric acid mono[2-(N'-[(R)-pyrrolidin-3-carbonyl]-hydrazinocarbonyl)-7-oxo-1,6-diaza-bicyclo[3.2.1]oct-6-yl] ester, or stereoisomer or pharmaceutically acceptable salt thereof.

13. A method for preventing or treating a bacterial infection comprising administering to a subject in need thereof an effective amount of the pharmaceutical composition according to anyone of claims 1, 2, 6, 7, 10, 11, and 12.

14. A method for treating or preventing a bacterial infection comprising administering to a subject in need thereof an effective amount of: (a) ertapenem, or a pharmaceutically acceptable salt thereof, and (b) a compound of Formula (I):

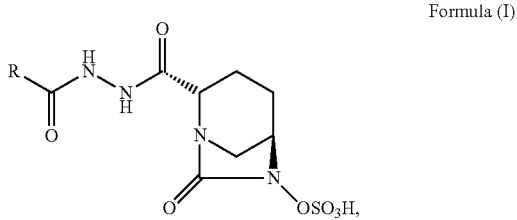

Formula (I)

or a stereoisomer or a pharmaceutically acceptable salt thereof, wherein R is piperidine or pyrrolidine.

15. The method according to claim 14, wherein the compound of Formula (I), or stereoisomer or pharmaceutically acceptable salt thereof, is administered in an amount from about 0.25 gram to about 4 grams per gram of the ertapenem, or pharmaceutically acceptable salt thereof.

16. The method according to claim 14, wherein the compound of Formula (I) or stereoisomer or pharmaceutically acceptable salt thereof, is administered in an amount from about 0.01 gram to about 10 grams.

17. The method according to claim 14, wherein the ertapenem, or pharmaceutically acceptable salt thereof, is administered in an amount from about 0.01 gram to about 10 grams.

18. The method according to claim 14, wherein the ertapenem, or pharmaceutically acceptable salt thereof, and the compound of Formula (I), or stereoisomer or pharmaceutically acceptable salt thereof, is administered in any of the following amounts:
  (i) about 0.25 gram of the compound of Formula (I), or stereoisomer or pharmaceutically acceptable salt thereof, and about 0.5 gram of the ertapenem, or pharmaceutically acceptable salt thereof;
  (ii) about 0.5 gram of the compound of Formula (I), stereoisomer or pharmaceutically acceptable salt thereof, and about 0.5 gram of the ertapenem, or pharmaceutically acceptable thereof;
  (iii) about 1 gram of the compound of Formula (I), or stereoisomer or pharmaceutically acceptable salt thereof, and about 0.5 gram of the ertapenem, or pharmaceutically acceptable salt thereof;
  (iv) about 0.25 gram of the compound of Formula (I), or stereoisomer or pharmaceutically acceptable salt thereof, and about 1 gram of the ertapenem, or pharmaceutically acceptable salt thereof;
  (v) about 0.5 gram of the compound of Formula (I), or stereoisomer or pharmaceutically acceptable salt thereof, and about 1 gram of the ertapenem, or pharmaceutically acceptable salt thereof;
  (vi) about 1 gram of the compound of Formula (I), or stereoisomer or pharmaceutically acceptable salt thereof, and about 1 gram of the ertapenem, or pharmaceutically acceptable salt thereof;
  (vii) about 2 grams of the compound of Formula (I), or stereoisomer or pharmaceutically acceptable salt thereof, and about 1 gram of the ertapenem, or pharmaceutically acceptable salt thereof;
  (viii) about 0.25 gram of the compound of Formula (I), or stereoisomer or pharmaceutically acceptable salt thereof, and about 2 grams of the ertapenem, or pharmaceutically acceptable salt thereof;
  (ix) about 0.5 gram of the compound of Formula (I), or stereoisomer or pharmaceutically acceptable salt thereof, and about 2 grams of the ertapenem, or pharmaceutically acceptable salt thereof;
  (x) about 1 gram of the compound of Formula (I), or stereoisomer or pharmaceutically acceptable salt thereof, and about 2 grams of the ertapenem, or pharmaceutically acceptable salt thereof; or
  (xi) about 2 grams of the compound of Formula (I), or stereoisomer or pharmaceutically acceptable salt thereof, and about 2 grams of the ertapenem, or pharmaceutically acceptable salt thereof.

19. The method according to claim 14, wherein the compound of Formula (I), or stereoisomer or pharmaceutically acceptable salt thereof, is administered before administration of the ertapenem, or pharmaceutically acceptable salt thereof.

20. The method according to any one of claims 14-19, wherein the compound of Formula (I), is:
  (a) trans-sulfuric acid mono-[2-(N'-[(R)-pyrrolidin-3-carbonyl]-hydrazinocarbonyl)-7-oxo-1,6-diaza-bicyclo [3.2.1]oct-6-yl] ester ;
  (b) (2S,5R) sulfuric acid mono-[2-(N'-[(R)-pyrrolidin-3-carbonyl]-hydrazinocarbonyl)-7-oxo-1,6-diaza-bicyclo [3.2.1]oct-6-yl] ester;
  (f) trans-sulphuric acid mono-[2-(N'-[(R)-piperidin-3-carbonyl]-hydrazinocarbonyl)-7-oxo-1,6-diaza-bicyclo [3.2.1]oct-6-yl] ester;
  (g) (2S,5R)-sulphuric acid mono-[2-(N'-[(R)-piperidin-3-carbonyl]-hydrazinocarbonyl)-7-oxo-1,6-diaza-bicyclo [3.2.1]oct-6-yl] ester;
  or
  a stereoisomer or a pharmaceutically acceptable salt thereof.

21. A method for increasing antibacterial effectiveness of ertapenem, or a pharmaceutically acceptable salt thereof, comprising co-administering to a subject in need thereof said ertapenem, or pharmaceutically acceptable salt thereof, with a compound of Formula (I):

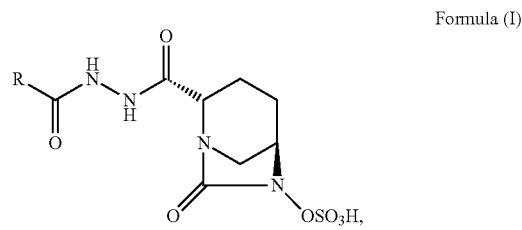

Formula (I)

or a stereoisomer or a pharmaceutically acceptable salt thereof, wherein R is piperidine or pyrrolidine.

22. The method according to claim 21, wherein the compound of Formula (I), or stereoisomer or pharmaceutically acceptable salt thereof, is administered in an amount from about 0.25 gram to about 4 grams per gram of the ertapenem, or pharmaceutically acceptable salt thereof.

23. The method according to claim 11, wherein the compound of Formula (I), or stereoisomer or pharmaceutically acceptable salt thereof, is administered after administration of the ertapenem, or pharmaceutically acceptable salt thereof.

24. The method according to claim 14, wherein the compound of Formula (I), or stereoisomer or pharmaceutically acceptable salt thereof, is administered simultaneously with administration of the ertapenem, or pharmaceutically acceptable salt thereof.

* * * * *